(12) United States Patent
Van Der Ende

(10) Patent No.: US 7,912,182 B2
(45) Date of Patent: *Mar. 22, 2011

(54) MEDICAL DIAGNOSTIC X-RAY APPARATUS PROVIDED WITH A COOLING DEVICE

(75) Inventor: Adrianus Van Der Ende, Son en Breugel (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/526,638

(22) PCT Filed: Feb. 12, 2008

(86) PCT No.: PCT/IB2008/050501
§ 371 (c)(1),
(2), (4) Date: Aug. 11, 2009

(87) PCT Pub. No.: WO2008/099337
PCT Pub. Date: Aug. 21, 2008

(65) Prior Publication Data
US 2010/0027762 A1 Feb. 4, 2010

(30) Foreign Application Priority Data
Feb. 13, 2007 (EP) .................................... 07102251

(51) Int. Cl.
*H01J 35/10* (2006.01)
*H01J 35/12* (2006.01)

(52) U.S. Cl. ........................................ 378/141; 378/199

(58) Field of Classification Search ................. 378/119, 378/121, 141, 193, 199, 200
See application file for complete search history.

(56) References Cited

U.S. PATENT DOCUMENTS

| | | | |
|---|---|---|---|
| 4,384,360 A | 5/1983 | Kitadate et al. | |
| 4,651,338 A * | 3/1987 | Hahn | 378/199 |
| 4,866,743 A * | 9/1989 | Kroener | 378/4 |
| 4,969,167 A * | 11/1990 | Zupancic et al. | 378/19 |
| 5,012,505 A * | 4/1991 | Zupancic et al. | 378/130 |
| 5,610,968 A * | 3/1997 | Deucher et al. | 378/199 |
| 7,236,571 B1 * | 6/2007 | Kendall et al. | 378/141 |
| 7,486,774 B2 * | 2/2009 | Cain | 378/136 |
| 2002/0071523 A1 | 6/2002 | Busse et al. | |
| 2004/0114723 A1 | 6/2004 | Ray et al. | |
| 2004/0196959 A1 * | 10/2004 | Weston | 378/141 |

FOREIGN PATENT DOCUMENTS

| | | |
|---|---|---|
| DE | 4217874 A1 | 12/1993 |
| DE | 29510801 U1 | 10/1995 |
| DE | 19824008 A1 | 12/1999 |
| DE | 10319735 A1 | 12/2004 |
| EP | 0182040 B1 | 5/1986 |
| JP | 2004358211 A | 12/2004 |
| WO | 205048843 A1 | 6/2005 |

\* cited by examiner

*Primary Examiner* — Edward J Glick
*Assistant Examiner* — Anastasia Midkiff

(57) ABSTRACT

The invention relates to a medical diagnostic X-ray apparatus (1) comprising an X-ray source (13), a hollow carrier (5) to which the X-ray source is connected, and a cooling mechanism (3) provided with a cooling means to cool the X-ray source (13) during use of the X-ray apparatus (1). The cooling construction (3) extends completely inside the hollow carrier (5) thus reducing the risk of leakage of cooling means.

20 Claims, 4 Drawing Sheets

MEDICAL DIAGNOSTIC X-RAY APPARATUS PROVIDED WITH A COOLING DEVICE

FIELD OF THE INVENTION

The invention relates to a medical diagnostic X-ray apparatus comprising:
an X-ray source,
a hollow carrier to which said X-ray source is connected,
and a cooling device containing a cooling agent for cooling the X-ray source during operation of the X-ray apparatus.

BACKGROUND OF THE INVENTION

A medical diagnostic X-ray apparatus of the type mentioned in the opening paragraph is known from German Utility Model DE 295 10 802 U1. The known X-ray apparatus is an X-ray apparatus which is suitable for surgical applications. This X-ray apparatus is provided with a C-arc as a hollow carrier to which the X-ray source is connected, and has a cooling device comprising a double-walled envelope of the X-ray source. A cooling agent flows through the double-walled envelope of the X-ray source, said cooling agent being supplied through cooling agent conduits and being discharged by a cooling unit located outside the C-arc. The cooling unit, the cooling agent, the cooling agent conduits and the double-walled envelope of the X-ray source form part of the cooling device of the known X-ray apparatus.

During operation of an X-ray apparatus, the production of X-rays by the X-ray source causes the generation of much heat. If this heat is not dissipated, the temperature of the X-ray source increases and eventually also the temperature of the rest of the X-ray apparatus increases. If the temperature of the X-ray source exceeds a certain threshold value, the X-ray apparatus is automatically switched off for safety reasons and the temperature of the X-ray source first has to decrease to a value below said threshold value before the X-ray apparatus can be switched on again. In order to ensure that, in comparison with X-ray apparatus without a cooling device, a longer, uninterrupted time of operation of an X-ray apparatus is possible, the known X-ray apparatus is provided with a cooling device.

For surgical applications very strict rules apply as regards the hygiene in treatment rooms, so that patients with open wounds cannot be infected by pathogens and the like. The use of X-ray apparatus with a cooling device causing air or another cooling agent to be blown into the treatment room is therefore not allowed. In the known X-ray apparatus which is suitable for surgical applications, the X-ray source is cooled by means of a cooling device having a double-walled envelope of the X-ray source through which a cooling agent flows. A cooling unit located outside the C-arc ensures that the cooling agent is first passed through a first cooling agent conduit, which extends partly via the inside of the C-arc, and then supplied to the double-walled envelope of the X-ray source. There the cooling agent absorbs part of the heat generated by the X-ray source during the production of X-rays and, subsequently, the cooling agent is carried away again to the cooling unit through a second cooling agent conduit which extends partly through the C-arc.

In order to be able to correctly position the X-ray source with respect to a patient, without the position of the X-ray source varying during operation of the X-ray apparatus, the C-arc is accurately balanced. A mass-change of the C-arc can disturb this delicate balance. In order to keep the disturbance of the balance of the C-arc to a minimum, as compared to an X-ray apparatus without a cooling device, the mass increase of the C-arc is kept as small as possible in the case of the known X-ray apparatus. To achieve this, the cooling unit is placed outside the C-arc and, as compared to an X-ray apparatus without a cooling device, an increase of the mass of the C-arc is caused only by the double-walled envelope of the X-ray source, the cooling agent conduits, insofar as they are situated in the C-arc, and the cooling agent present in the cooling agent conduits in the C-arc.

A drawback of the known X-ray apparatus suitable for surgical applications and provided with a cooling device having a double-walled envelope of the X-ray source, the cooling unit of which is situated outside the C-arc, resides in that the use of this cooling device involves the risk of leakage of cooling agent. The reason for this being that the connections of the cooling agent conduits to the cooling unit and the double-walled envelope of the X-ray source are a weak point in the construction of the known cooling device, and particularly the connections of the cooling agent conduits to the cooling unit located outside the C-arc can become detached during operation of the X-ray apparatus, causing cooling agent to leak into the treatment room.

SUMMARY OF THE INVENTION

It is an object of the invention to provide a medical diagnostic X-ray apparatus of the type mentioned in the opening paragraph, which is provided with a cooling device having a reduced risk of leakage of cooling agent as compared to the cooling device of the known X-ray apparatus.

The object is achieved by a medical diagnostic X-ray apparatus in accordance with the invention, which is characterized in that the cooling device extends entirely within the carrier. The cooling device comprising a cooling agent circulating exclusively within the carrier cools the X-ray source in that the cooling agent absorbs the heat generated during the production of X-rays. Subsequently, this cooling agent transmits the heat absorbed to the carrier which subsequently transmits the heat to the surroundings of the X-ray apparatus. As the cooling device extends exclusively within the hollow carrier, the cooling device in accordance with the invention does not have any connections of the cooling agent conduits which extend outside the carrier and which can become detached during operation of the X-ray apparatus with the associated risk of cooling agent leaking into the treatment room.

An additional advantage is that the X-ray apparatus in accordance with the invention does not have cooling agent conduits which extend, at least partly, outside the carrier. After all, this means that during operation of the X-ray apparatus, mechanical stress cannot build up in the cooling agent conduits, which stress adversely affects the balance of the carrier, causing the position of the X-ray source to change with respect to a patient during operation of the X-ray apparatus. In addition, by virtue of the absence of cooling agent conduits extending, at least partly, outside the carrier, the accessibility of the X-ray apparatus is increased for both patients and medical staff. This is of particular importance if the X-ray apparatus is used in a space of limited dimensions, such as a treatment room.

A preferred embodiment in accordance with the invention is a medical diagnostic X-ray apparatus, characterized in that the cooling device extends substantially within the entire carrier. By virtue thereof, the heat generated during the production of X-rays and absorbed by the cooling agent can be transmitted to the entire carrier which subsequently transmits the heat to the surroundings of the X-ray apparatus. By virtue of the fact that not only a small part of the carrier, but rather the entire carrier can absorb the heat originating from the X-ray source, and can transmit said heat to the surroundings, the total heat capacity and the total radiation surface of the carrier are used, as a result of which very efficient cooling of the X-ray apparatus is achieved. It is to be noted that, under certain conditions, a securing piece for securing the X-ray source to the carrier, or for securing a detector suitable for detecting X-radiation to the carrier, may form part of the carrier.

A further preferred embodiment in accordance with the invention is a medical diagnostic X-ray apparatus, which is characterized in that the cooling agent is in direct thermal contact with the carrier. By bringing the cooling agent in direct thermal contact with the carrier, and by dispensing with the use of cooling agent conduits extending substantially within the entire carrier, the efficiency of the heat transfer between the cooling agent and the carrier is increased and further improved cooling of the X-ray apparatus is achieved.

Further improved cooling of the X-ray apparatus is achieved if the carrier is provided with an internal partition which creates at least two channels through which the cooling agent can circulate through the carrier. An example of such an internal partition is a partitioning wall extending in the carrier and parallel to the carrier, which partitioning wall is provided with at least two openings for the circulation of the cooling agent, so that the individual channels are in direct communication with each other. Preferably one of the at least two openings in the partitioning wall is situated in the direct vicinity of the X-ray source at one end of the carrier, and the second opening is preferably situated in the direct vicinity of the other end of the carrier.

A still further preferred embodiment in accordance with the invention is a medical diagnostic X-ray apparatus, which is characterized in that the cooling agent is air.

An advantage of the use of air as the cooling agent is that air is already present in the hollow carrier and that there is no need for a separate cooling agent. By virtue thereof, the cooling device is not only simpler than a cooling device using a separate cooling agent but also cheaper.

Another advantage of the use of air as a cooling agent is that air is a light cooling agent. In order to cause air to circulate through the carrier, there is no need for a heavy expensive pump as would be necessary, for example, in the case of oil or water as a cooling agent; instead the use of a fan is sufficient. By virtue thereof, the cooling device is not only cheaper than a cooling device using a heavy, expensive pump, but, by virtue of the light cooling agent and the fan, it is also substantially lighter than a cooling device making use of a heavier cooling agent and a heavy, expensive pump, and, in addition, the balancing of the carrier is much less adversely affected than in the case of a cooling device using a heavier cooling agent than air and a heavy, expensive pump.

An embodiment in accordance with the invention is a medical diagnostic X-ray apparatus, which is characterized in that the cooling device is provided with an envelope, the X-ray source being located within the envelope. The envelope provides a large radiation surface, so that the heat generated during the production of X-rays by the X-ray source situated within the envelope can be transmitted more efficiently, by means of the large radiation surface, to the rest of the cooling device and ultimately to the surroundings of the X-ray apparatus. The envelope may additionally comprise a further cooling agent. Transformer oil would be a practical choice for the further cooling agent, because transformer oil has a very poor electrical conductivity, as a result of which breakdown of the high voltage of the X-ray source is precluded. Of course, within the envelope, other cooling agents can also be used. The envelope within which the X-ray source is located does not only increase the efficiency of the cooling device of the X-ray apparatus, but also has the practical advantage that it keeps the further cooling agent in the direct vicinity of the X-ray source and that, if the X-ray source must be replaced, replacement can include replacement of the envelope, so that the risk of leakage of the further cooling agent comprised in the envelope is minimal.

A further embodiment in accordance with the invention is a medical diagnostic X-ray apparatus, which is characterized in that the envelope is provided with cooling ribs. The use of cooling ribs causes the surface of the envelope around the X-ray source to be increased, leading to a further increase of the efficiency of the cooling device of the X-ray apparatus.

BRIEF DESCRIPTION OF THE DRAWINGS

These and other aspects of the invention will be further elucidated with reference to the drawings, wherein:

FIG. 4 is a qualitative view of the temperature of the X-ray source as a function of the time during which the X-ray source is in operation, said X-ray source forming part of:

a) a medical diagnostic X-ray apparatus without a cooling device, b) a medical diagnostic X-ray apparatus provided with a cooling device in accordance with the invention, without an envelope of the X-ray source, and a medical diagnostic X-ray apparatus provided with a cooling device in accordance with the invention, comprising an envelope of the X-ray source that is provided with cooling ribs, and said envelope containing a further cooling agent.

DETAILED DESCRIPTION OF THE INVENTION

Figure 1:
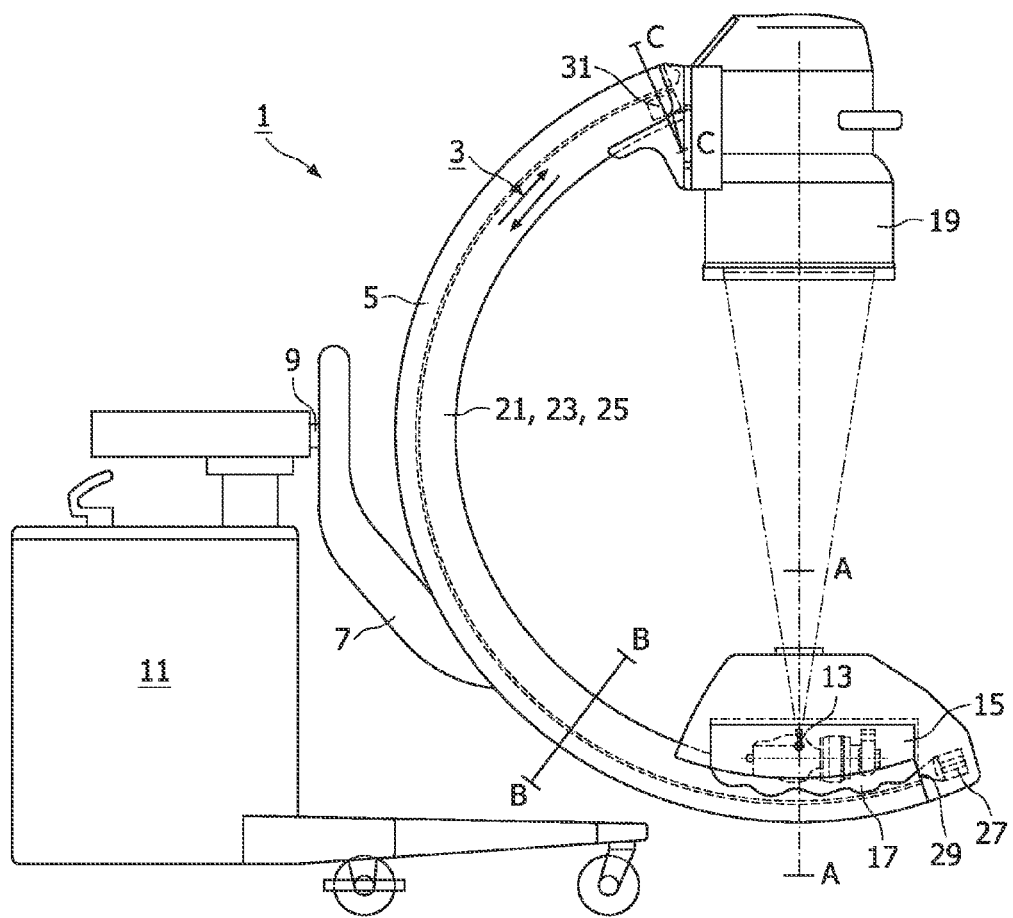
FIG. 1 is a diagrammatic side view of an exemplary embodiment of a medical diagnostic X-ray apparatus in accordance with the invention.

FIG. 1 is a diagrammatic side view of an exemplary embodiment of a medical diagnostic X-ray apparatus 1 provided with a cooling device 3 in accordance with the invention. In the exemplary embodiment shown, the X-ray apparatus 1 is provided with a rotatable carrier, i.e. a C-arc 5, and a frame 7 which guides the C-arc and with respect to which the C-arc 5 can be rotated. The frame 7 is rotatable about a horizontal shaft 9 and is connected, via this shaft 9, to a stand 11 which is movably located on the floor. At one end of the C-arc 5 there is an X-ray source 13 that is situated within an envelope 15 provided with cooling ribs 17. An X-radiation detector 19, in this case an image amplifier, is attached to the other end of the C-arc 5 so as to be diametrically opposite the X-ray source 13. By rotating the frame 7 about the horizontal shaft 9, and by rotating the C-arc 5 with respect to the frame 7, the X-ray source 13 and the X-radiation detector 19 can be positioned relative to a patient, such that the part of the patient to be examined is situated between the X-ray source 13 and the X-radiation detector 19. The C-arc 5 is provided on the inside with two channels 21 and 23 which are separated from each other by a thin partitioning wall 25, and through which channels the air present in the C-arc 5 circulates as a cooling agent. The arrows in FIG. 1 indicate that the direction of circulation of the air through channel 21 is opposite to the direction of circulation of the air through channel 23. At the end of the C-arc 5 where the X-ray source 13 is situated, a fan 27 is arranged inside the C-arc 5, which fan brings about the actual circulation of air as a cooling agent through the C-arc 5. The exact location of the fan 27 is not relevant, therefore it could also be arranged, if necessary, in the direct vicinity of the X-radiation detector 19. The thin partitioning wall 25 between the channels 21 and 23 has at least two openings 29 and 31 for the circulation of the cooling agent, so that the individual channels 21 and 23 are in direct communication with each other. Opening 29 is in the direct vicinity of the X-ray source 13 at one end of the C-arc 5, and opening 31 is situated in the direct vicinity of the X-radiation detector 19 at the other end of the C-arc 5. In addition to the air in the carrier 5 functioning as a cooling agent, the individual channels 21 and 23, the partitioning wall 25, the fan 27 and the openings 29 and 31, also the envelope 15 provided with cooling ribs 17, within which envelope the X-ray source 13 is arranged and which is provided with a further coolant, form part of the cooling mechanism 3 shown in FIG. 1.

It is of course possible to use another gas or a liquid as the cooling agent instead of air. However, it has been found in practice that substitution of air with another gas as the cooling agent hardly results in better cooling of the X-ray source 13. In addition, the use of another gas as the cooling agent is generally more expensive than air, because the other gas, unlike the air already present in the C-arc 5, first has to be introduced into the C-arc 5. In addition, the use of a gas other than air entails the risk that, for example in the case of a repair to the C-arc 5, the gas leaks out of the C-arc 5, so that the C-arc 5 has to be refilled, at some point in time, with the gas used as the coolant. The use of a liquid as the cooling agent instead of air, however, does lead to better cooling of the X-ray source 13. In that case, the fan 27 has to be replaced by a pump unit which causes the liquid to circulate through a closed circuit extending entirely in the C-arc 5. However, by using a liquid instead of air as the cooling agent, the X-ray device 1 becomes much more expensive, because the liquid must first be introduced into the C-arc 5 and a liquid is more expensive than air. Besides, the use of a liquid instead of air as the cooling agent causes the weight of the C-arc 5 to increase substantially, which is detrimental to the balancing of the C-arc 5. Furthermore, repairs to the C-arc 5 and changing the X-ray source become much more difficult if a liquid is used as the cooling agent instead of air.

In practice, the X-ray source 13 is almost always situated in an envelope 15 filled with transformer oil, because this oil has a very poor electrical conductivity, so that breakdown of the high voltage of the X-ray source is precluded. The process of filling oil into the envelope 15 is expensive, so that in the case of wear of the X-ray source 13, the X-ray source is always replaced together with the envelope 15 filled with the transformer oil. In practice, in the cooling device for cooling the X-ray source, two separate cooling concepts are employed, that is to say, air and transformer oil are used as the cooling agent, so that the X-ray source can be readily replaced without the need to work with oil in a treatment room, such as an operation theater in a hospital.

Figure 2:
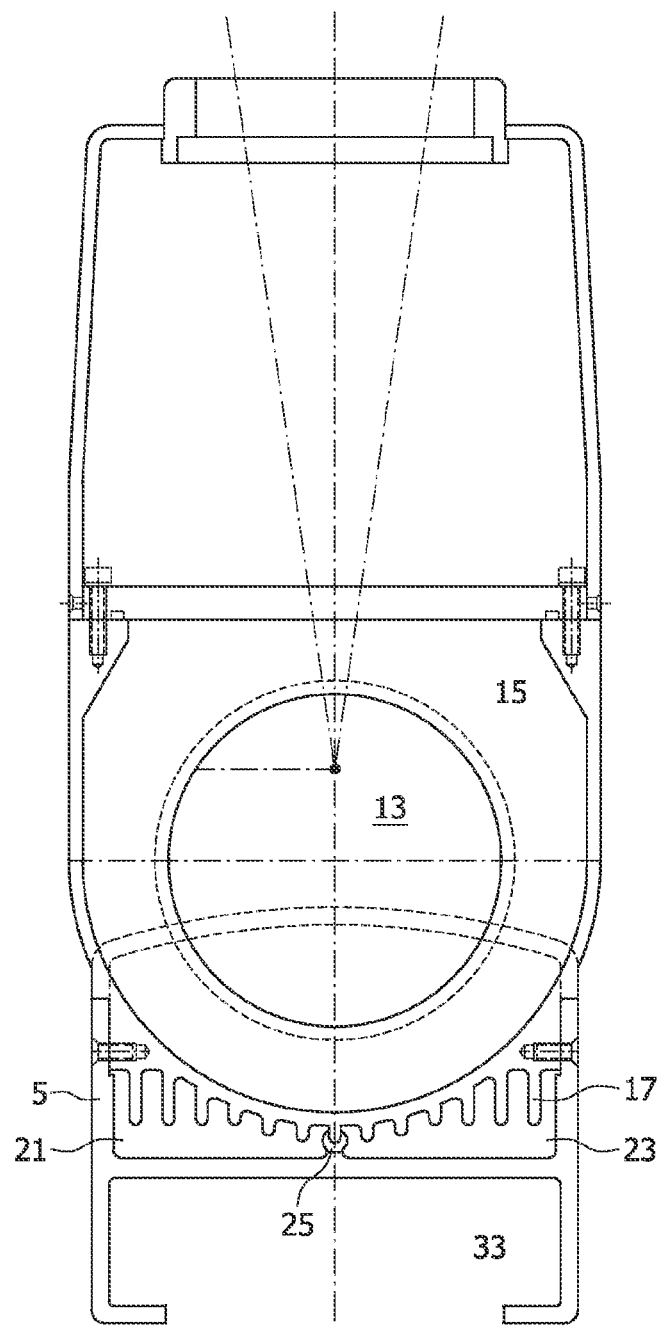
FIG. 2 is a diagrammatic cross-sectional view taken on the line A-A in FIG. 1.

FIG. 2 is a diagrammatic cross-sectional view taken on the line A-A in FIG. 1 and shows the separate channels 21 and 23 through which air circulates as the cooling agent, and the thin partitioning wall 25 which separates the channels 21 and 23 from each other. In the simplest case, in which the X-ray source 13 is not surrounded by an envelope, air is supplied to the X-ray source 13 via the channel 21 in order to absorb the heat produced by the X-ray source 13 during the production of X-radiation. Via the channel 23, the air that has absorbed the heat from the X-ray source 13 is removed from the X-ray source 13 and the absorbed heat is transferred to the C-arc 5 before the air is supplied again to the X-ray source 13 via channel 21.

However, in FIG. 2 the X-ray source 13 is surrounded by an envelope 15 provided with cooling ribs 17. The envelope 15 is filled with transformer oil which, in addition to air in the C-arc 5, serves as a further cooling agent for the X-ray apparatus 1. The transformer oil absorbs the heat generated by the X-ray source 13 during the production of X-radiation. This heat is subsequently transmitted to the air in channel 23 serving as a cooling agent, which air subsequently transmits the heat to the C-arc 5 which, in turn, transfers the heat to the surroundings of the X-ray apparatus 1. The cooling ribs 17 of the transformer oil-filled envelope 15 of the X-ray source 13 create a larger radiation surface of the envelope, thereby improving the efficiency of the cooling device of the X-ray apparatus. Channel 33, which, like the channels 21 and 23, is situated in the C-arc 5, but through which no cooling agent circulates, engages the frame 7 and its importance lies in the fact that it enables the C-arc 5 to rotate with respect to the frame 7.

Figure 3A:
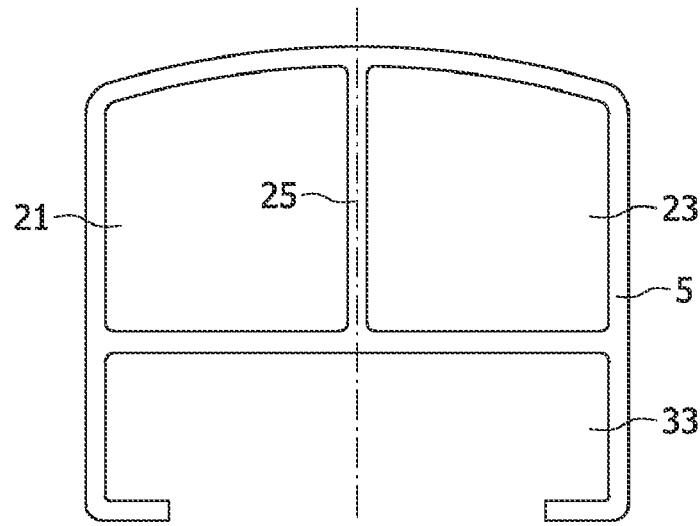
FIG. 3a is a diagrammatic cross-sectional view taken on the line B-B in FIG. 1.

FIG. 3a is a diagrammatic cross-sectional view of the C-arc 5 taken on the line B-B in FIG. 1, in which the separate channels 21 and 23 are shown through which the air functioning as the cooling agent is circulated. The channels 21 and 23 are separated from each other by the thin wall 25. Channel 33, through which no cooling agent circulates, engages frame 7 and is important in that it enables the C-arc 5 to be rotated with respect to the frame 7.

Figure 3B:
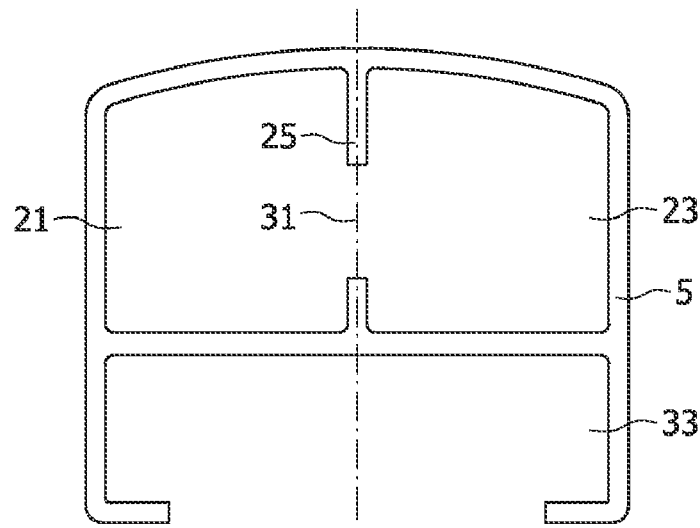
FIG. 3b is a diagrammatic cross-sectional view taken in the line C-C in FIG. 1.

For comparison with FIG. 3a showing a diagrammatic cross-sectional view taken on the line B-B in FIG. 1, FIG. 3b diagrammatically shows a cross-sectional view of the C-arc 5 taken on the line C-C in FIG. 1. In this Figure, like in FIG. 3a, the separate channels 21 and 23, the thin wall 25 and the channel 33 are shown. However, unlike FIG. 3a, the thin wall 25 in FIG. 3b is provided with an opening 31 which allows the channels 21 and 23 to be in direct communication with each other and through which the air can pass from one channel to the other channel.

Figure 4:
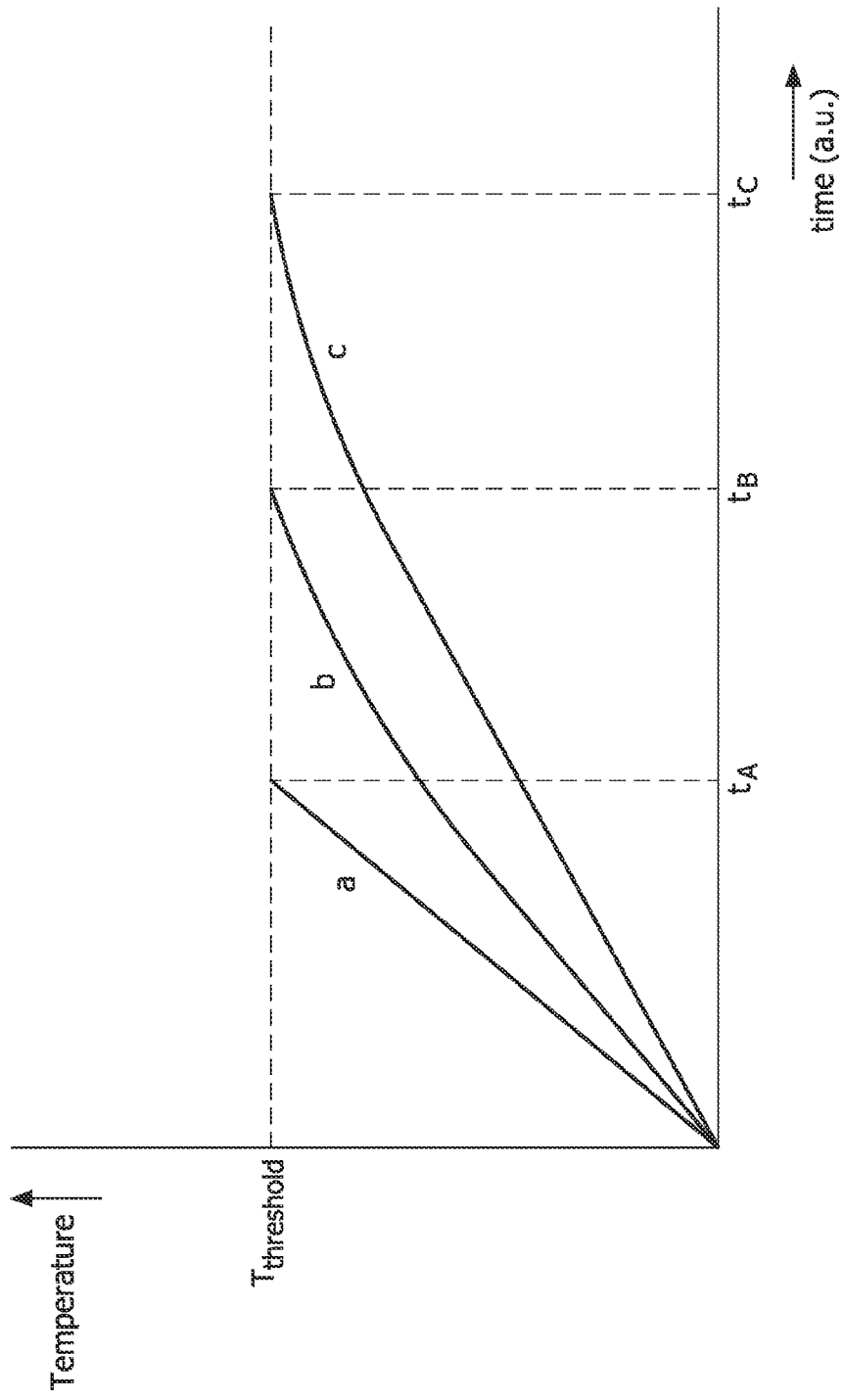

FIG. 4 is a qualitative view of the temperature of the X-ray source as a function of the time during which the X-ray source is in operation, said X-ray source forming part of:

a) a medical diagnostic X-ray apparatus without a cooling device, b) a medical diagnostic X-ray apparatus provided with a cooling device in accordance with the invention, without an envelope of the X-ray source, and a medical diagnostic X-ray apparatus provided with a cooling device in accordance with the invention, comprising an envelope of the X-ray source that is provided with cooling ribs, the envelope containing a further cooling agent.

In FIG. 4, the temperature T of the X-ray source is plotted along the vertical axis. Also the threshold value for the temperature of the X-ray source, $T_{threshold}$, is plotted along the vertical axis, $T_{threshold}$ being the temperature above which the X-ray apparatus is automatically switched-off for safety reasons. By setting such a threshold value of the temperature, it is precluded that medical staff or patients can come into contact with hot parts of the X-ray apparatus. In FIG. 4, time in random units is plotted along the horizontal axis. The point in time $t_A$ indicates how long it takes before an X-ray source in a medical diagnostic X-ray apparatus without a cooling device has reached the threshold for the temperature. The point in time $t_B$ indicates how long it takes before the threshold value for the temperature of the X-ray source is attained if the X-ray source forms part of a medical diagnostic X-ray apparatus provided with a cooling device in accordance with the invention, but without an envelope of the X-ray source. The qualitative view of FIG. 4 clearly shows that the time it takes before the threshold value of the temperature of the X-ray source is attained is substantially longer if the X-ray source forms part of an X-ray apparatus provided with a cooling device in accordance with the invention, as compared with the situation in which the X-ray source forms part of an X-ray apparatus which is not provided with a cooling device for cooling the X-ray source. In other words, FIG. 4 clearly shows that $t_B$ is much larger than $t_A$, which means that the period of time during which a medical diagnostic X-ray apparatus provided with a cooling device in accordance with the invention can be used without interruption before being switched off automatically for safety reasons is much longer than that of a medical diagnostic X-ray apparatus without a cooling device for the X-ray source.

If the X-ray source forms part of an X-ray apparatus comprising a cooling device in accordance with the invention including an envelope with cooling ribs enveloping the X-ray source, the envelope containing a further cooling agent, then the improvement of the efficiency of the cooling device is such that the X-ray apparatus can be used without interruption for a period of time $t_C$. In practice it has even been found possible to attain an uninterrupted period of operation of the X-ray apparatus which is twice as long as that of an X-ray apparatus without a cooling device.

The invention is particularly suitable for surgical applications, as in this case, due to the strict rules regarding hygiene in treatment rooms, air is not allowed to be blown into the treatment room. Apart from stationary X-ray apparatus, the invention is also relevant for mobile X-ray apparatus for surgical applications.

The invention makes it possible for medical staff to perform their duties without any, or with much less, interruptions than before, without there being a risk of leakage of the cooling agent during operation of the X-ray apparatus. The invention also enables interventions to be performed without interruption for a longer period of time than was previously possible. Besides, the invention is very practical, as there is a tendency towards patients gradually getting fatter. The fatter a patient is, the higher the degree of absorption and scattering of X-radiation, and the larger the power of the X-ray source must be in order to be able to produce qualitatively good images of a patient. As the power of the X-ray source increases, more heat is generated during the production of X-radiation by the X-ray source, and the threshold value for the temperature at which the X-ray apparatus is automatically switched off for safety reasons is reached sooner. The invention makes it possible, also in the case of fat patients, to achieve a sufficiently long uninterrupted period of operation of the X-ray apparatus.

The invention claimed is:

1. A medical diagnostic X-ray apparatus comprising:
   an X-ray source;
   a hollow carrier of said source, said carrier elongated so as to extend between two ends; and,
   extending from one of said ends of the carrier to the other, an elongated cooling device comprising, for cooling said source, both cooling agent and at least one of a circulation producer for providing mechanical force to cause circulation of said agent and a circulation director for providing directionality in flow of said agent, said device being located entirely within said carrier without need for an inlet for, during operation of said apparatus, supplying said agent from outside said carrier, and without need for an outlet to, during said operation, output said agent to outside said carrier.

2. A medical diagnostic X-ray apparatus as claimed in claim 1, wherein said device extends substantially within the entire carrier.

3. A medical diagnostic X-ray apparatus as claimed in claim 1, wherein said carrier and said device arc configured for reliance on said carrier for cooling said agent by virtue of said agent being in direct thermal contact with said carrier.

4. A medical diagnostic X-ray apparatus as claimed in claim 3, wherein said agent is air.

5. A medical diagnostic X-ray apparatus as claimed in claim 1, wherein said device is provided with an envelope, the X-ray source being arranged within the envelope.

6. A medical diagnostic X-ray apparatus as claimed in claim 5, wherein the envelope is provided with cooling ribs.

7. The apparatus of claim 1, said device comprising both said circulation producer and said circulation director.

8. The apparatus of claim 1, said circulation producer comprising a structure that serves as at least one of a fan and a pump.

9. The apparatus of claim 1, said device being configured for oppositely directed flows of said agent along, but within, said carrier.

10. The apparatus of claim 9, said circulation director comprising a partition for separating one of said flows from the other of said flows, said one flow being along one side of said partition, said other flow being along an opposite side of said partition.

11. The apparatus of claim 10, said partition having, at each of said ends, a respective opening for circulating said agent back within said carrier.

12. The apparatus of claim 10, said partition serving in defining a channel configured for rotation of said carrier.

13. The apparatus of claim 1, said carrier being a C-arm.

14. The apparatus of claim 1, said device being located entirely within a hollow, radially-internal region of said carrier.

15. The apparatus of claim 1, configured for cooling that relies upon said carrier serving as a solid, cooling intermediary in that its internal surface is in direct thermal contact with said agent and its external surface is in direct thermal contact with air outside said apparatus.

16. The apparatus of claim 1, said carrier, at said one end, being configured for physically supporting said source and, at said other end, being configured for physically supporting an X-radiation detector.

17. An X-ray apparatus comprising:
   an X-ray source;
   a carrier for physically supporting said source, said carrier being elongated so as to extend between two ends; and
   exclusively internal to said carrier, a cooling device elongated so as to extend from one of said ends of the carrier to the other, said device comprising cooling agent and at least one of a circulation producer for providing mechanical force to cause circulation of said agent and a circulation director for providing directionality in flow of said agent, said device and said carrier being configured for said agent being circulated exclusively internally within said carrier to cool said agent by means of heat dissipation from said agent to outside said carrier.

18. The apparatus of claim 17, the configuring of said carrier configuring it hollow for accommodation of said device, said device comprising both said circulation producer and said circulation director.

19. A method for reducing risk of leakage of cooling agent from an X-ray apparatus comprising an X-ray source, comprising:

for a carrier for physically supporting said source, said carrier elongated so as to extend between two ends, disposing, exclusively internally within said carrier, a cooling device elongated so as to extend from one of said ends of the carrier to the other, said device comprising a circulation director for providing directionality in flow of cooling agent to circulate said agent within said carrier, the circulation being exclusively internally within said carrier to cool said agent by means of heat dissipation from said agent to outside said carrier.

20. The method of claim 19, said device further comprising a circulation producer for providing mechanical force to cause circulation of said agent, said director extending from said one end to said other end.

* * * * *